(12) United States Patent
Kluczynski

(10) Patent No.: US 7,800,764 B2
(45) Date of Patent: Sep. 21, 2010

(54) METHOD AND APPARATUS FOR REDUCING FRINGE INTERFERENCE OF LIGHT

(75) Inventor: Pawel Kluczynski, Västra Frölunda (SE)

(73) Assignee: Siemens Aktiengesellschaft, Munich (DE)

( * ) Notice: Subject to any disclaimer, the term of this patent is extended or adjusted under 35 U.S.C. 154(b) by 286 days.

(21) Appl. No.: 11/998,479

(22) Filed: Nov. 30, 2007

(65) Prior Publication Data

US 2008/0137084 A1 Jun. 12, 2008

(30) Foreign Application Priority Data

Nov. 30, 2006 (EP) .................................. 06024845

(51) Int. Cl.
*G01B 11/02* (2006.01)

(52) U.S. Cl. ...................................................... 356/519
(58) Field of Classification Search .................. 356/519
See application file for complete search history.

(56) References Cited

U.S. PATENT DOCUMENTS

| | | | |
|---|---|---|---|
| 3,809,457 A * | 5/1974 | Kurtz et al. .................. 359/455 |
| 4,684,258 A | 8/1987 | Webster | |
| 4,934,816 A | 6/1990 | Silver et al. | |
| 6,373,632 B1 * | 4/2002 | Flanders ...................... 359/578 |
| 6,806,967 B2 * | 10/2004 | Atia et al. .................... 356/519 |

* cited by examiner

*Primary Examiner*—Gregory J Toatley, Jr.
*Assistant Examiner*—Scott M Richey

(57) ABSTRACT

A method for reducing fringe interference of light created in a passive cavity defined by partially reflecting optical surfaces, wherein the optical path length of the cavity is varied with a Gaussian distribution, where the standard deviation is at least one-quarter of the light's wavelength.

16 Claims, 2 Drawing Sheets

METHOD AND APPARATUS FOR REDUCING FRINGE INTERFERENCE OF LIGHT

CROSS REFERENCE TO RELATED APPLICATIONS

This application claims priority of European Patent Office application No. 06024845.7 EP filed Nov. 30, 2006, which is incorporated by reference herein in its entirety.

FIELD OF INVENTION

The invention relates to a method for reducing fringe interference of light created in a passive cavity defined by partially reflecting optical surfaces, wherein the optical path length of the cavity is varied.

The invention further relates to a corresponding apparatus.

BACKGROUND OF INVENTION

Laser absorption spectroscopy offers high speed and high precision capabilities for detection of numerous trace gas species in gas mixtures at atmospheric pressure with a small cross sensitivity towards other gas components. Tunable diode laser spectrometers are particularly suited to high sensitivity studies, in part because they may be frequency modulated to reduce low frequency laser noise and electronic noise. A typical spectrometer includes a frequency tunable laser for generating a laser beam which passes through a sample cell containing the gas mixture and onto an optical detector. The signal received at the optical detector is demodulated to obtain an absorption induced signal.

Unfortunately, sensitivity is usually severely limited by the presence of interference fringes (etalon fringes) which appear as the narrow bandwidth laser is tuned through the range of the desired absorption signal. The interference fringes are attributable to laser frequency dependent interference between pairs of parallel optical surfaces which form a passive cavity or etalon (in contrast to the laser's active cavity) and through which the laser beam must pass as it propagates from the laser through the sample cell to the optical detector. The fringes may result from laser transmission through individual optical elements, such as windows or lenses, or through air and vacuum paths separated by the surfaces of different system elements. The reflections causing the interference fringes are extremely difficult to eliminate completely even with high quality anti-reflection coatings and careful optical alignment. These fringes, even when very weak, can easily overwhelm the absorption induced signal from the sample.

A number of different attempts have been made to reduce the etalon effects by means of mechanical variation of the etalon length in order to average out the etalon fringe pattern. U.S. Pat. No. 4,684,258 proposes insertion of a vibrating Brewster plate between two etalon creating surfaces and thus periodically changing the optical path length of the etalon. When the vibration frequency is asynchronous with other modulation frequencies, the fringe pattern due to etalon effects will be averaged out. U.S. Pat. No. 4,934,816 proposes a similar mechanical approach, where etalon effects in a multipass cell are reduced by introducing a vibrating mirror. Both approaches use a triangular waveform for modulation of the plate and mirror position, respectively. Triangular waveform offers better etalon fringe reduction compared to square or sinus waveforms since the time spent by the vibrating element at the turning points is minimized. Unfortunately, this approach has two drawbacks. Firstly, generation of a triangular waveform requires a broadband driver and imposes high requirements on the electromechanical setup. Secondly, in practice, the vibration amplitude of the element has to be more than 15 laser wavelengths to obtain a sufficient reduction of the etalon effect. This becomes especially impractical when the longer laser wavelengths are used thus imposing higher power consumption and putting higher demand on the mechanical components (for example, standard piezo-transducers have limited length expansion capabilities). Moreover, unwanted displacement/defocusing of the laser beam may appear when the position of the element oscillates with large amplitudes.

SUMMARY OF INVENTION

Therefore, the invention seeks to provide a more effective method and apparatus for reducing fringe interference.

According to the invention this is achieved by a method defined in an independent claim and also by an apparatus according to a further independent claim.

Preferred embodiments of the method and apparatus according to the invention are specified in the remaining claims.

In accordance with the invention the optical path length of the passive cavity is varied with a Gaussian distribution, where the standard deviation is at least one-quarter of the light's wavelength, preferably at least one-third wavelength and more preferably less than one wavelength. Thus, compared to the triangle modulation which needs vibration amplitudes over several laser wavelengths, an efficient etalon averaging is obtained already at amplitudes following a Gaussian (normal) distribution with a standard deviation slightly above one-quarter wavelength. Another advantage is that, due to character of noise modulation, there is no need of amplitude and phase control of the modulating waveform, thus allowing much simpler hardware design.

To vary the optical length of the cavity, one of the optical surfaces of the passive cavity may be moved or tilted back and forth or a tunable optical element may be placed in said passive cavity to increase the optical path length by an additional length wherein said optical element is tuned as to vary the additional length with said Gaussian distribution. The tunable optical element may be an additional etalon, the thickness of which or the index of the medium therein are varied by means of an electrodynamic, magnetostrictive, electrostatic or piezoelectric actuator, or by means of pressure or sound or the like imposed on the medium inside the etalon.

BRIEF DESCRIPTION OF THE DRAWINGS

The present invention will be now described, by way of example, with reference to the accompanying drawings, in which.

DETAILED DESCRIPTION OF INVENTION

Figure 1:
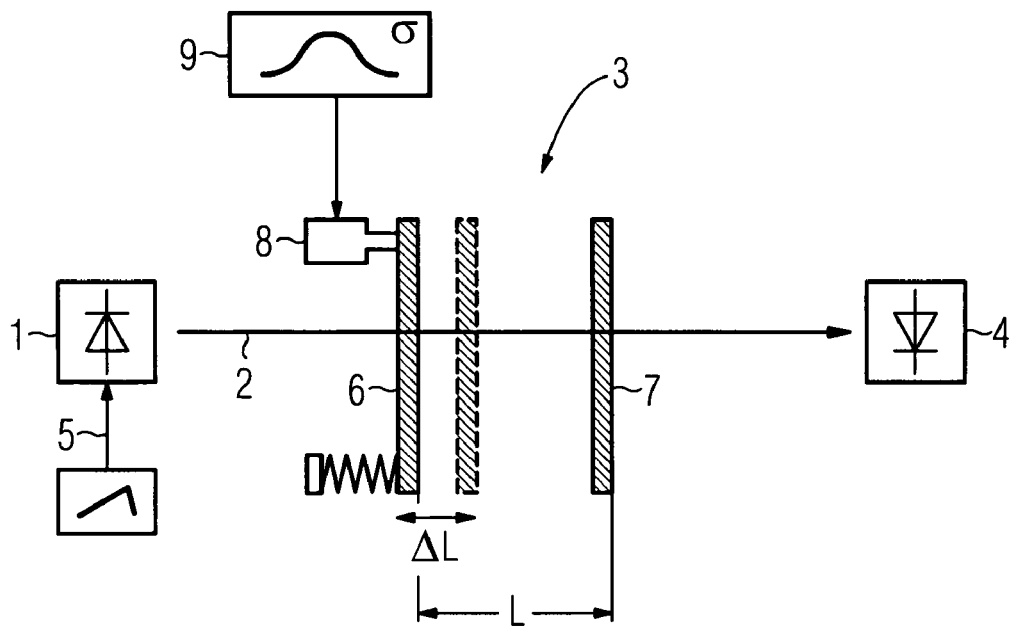
FIG. 1 is a schematic diagram of an apparatus for reducing fringe interference created in a passive cavity wherein the optical path length of the cavity is varied with a Gaussian distribution.

FIG. 1 shows, as an example for the apparatus according to the invention, a laser spectrometer including a frequency tunable laser 1 for generating a laser beam 2 which passes through an optical system 3 onto an optical detector 4. The optical system 3 comprises, inter alia, a sample cell (not shown) containing a trace gas species in a gas mixture. The laser 1 is modulated with a triangular signal 5 in order to sweep the laser wavelength across specific absorption lines of the trace gas to be determined. The signal received at the optical detector 4 is demodulated to obtain an absorption induced signal.

Partially reflecting optical surfaces of the sample cell and of other optical elements of the optical system 3, such as windows or lenses, form a passive optical cavity (etalon) which is here represented by a pair of plane parallel partially reflecting planes 6 and 7 at a distance L. This etalon may create the so-called etalon effect which is a dominating source of disturbing background signals in the laser spectrometer. When the reflected or scattered portions of the laser beam 2 reach the detector 4 and interfere with the primary beam 2, a periodic, wavelength dependent fringe pattern is created as the laser wavelength is scanned, which pattern obscures the absorption signal of interest. As a consequence, the accuracy of laser spectrometer is affected.

When the laser beam 2 propagates through the etalon, multiple reflections inside the etalon will give rise to standing waves, and in consequence the transmitted light intensity will vary periodically with the laser wavelength $\lambda$. According to Pawel Kluczynski and Ove Axner: "Theoretical Description Based on Fourier Analysis of Wavelength-Modulation Spectrometry in Terms of Analytical and Background Signals" in Applied Optics 38, 5803-5815 (1999), the transmission T through the etalon can be written for small reflectivities R<0.04 of the planes 6 and 7 as $$T(\lambda) = 1 - \frac{F}{2} + \frac{F}{2}\cos\left(2\pi\frac{2L}{\lambda}\right),$$

where $$F = \frac{4R}{1-R^2}$$

is the coefficient of finesse.

As the laser wavelength $\lambda$ is scanned by $\Delta\lambda$ from its nominal wavelength $\lambda_c$, the optical transmission T will follow a periodic pattern, the phase of which will depend on the total etalon length L, according to $$T(\lambda) = 1 - \frac{F}{2} + \frac{F}{2}\cos\left(2\pi\frac{2L}{\lambda_c} - 2\pi\frac{2L}{\lambda_c^2}\Delta\lambda\right),$$

where it is assumed that $\Delta\lambda \ll \lambda_c$

Figure 2:
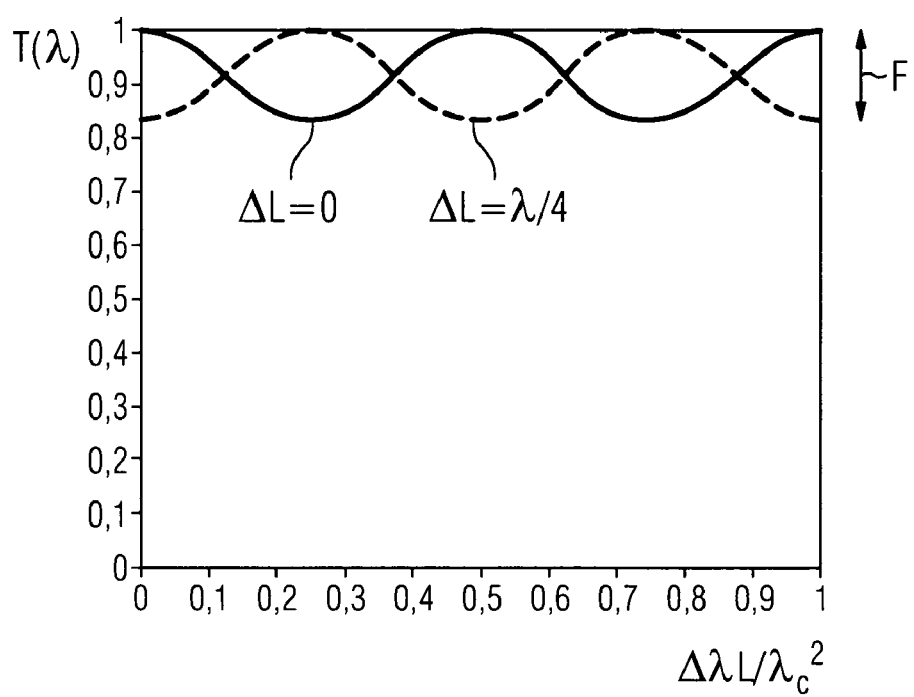
FIG. 2 illustrates the influence of the etalon effect on optical transmission.

If the etalon length L is changed exactly by $\Delta L = m \cdot \lambda/4$, where m is an odd number, the etalon fringe pattern will be reversed as shown in FIG. 2. Thus, by changing the etalon length L back and forth in a certain manner at given frequency and amplitude, the unwanted periodic fringe pattern can be averaged out yielding flat optical transmission.

According to the invention and as can be seen in FIG. 1, the optical path length of the etalon, here the etalon length L, is varied with a Gaussian distribution. For this purpose, a piezoelectric actuator 8 is coupled to one of the planes 6 and 7, here plane 6, which actuator 8 is driven by a Gaussian noise generator 9.

To vary the optical length L of the passive cavity (etalon), one of the optical surfaces of the optical system 3 may be moved or tilted back and forth or a tunable optical element may be placed in said passive cavity to increase the optical path length by an additional length wherein said optical element is tuned as to vary the additional length with said Gaussian distribution. The tunable optical element may be an additional etalon, the thickness of which or the index of the medium therein are varied by means of an electrodynamic, magnetostrictive, electrostatic or piezoelectric actuator, or by means of pressure or sound or the like imposed on the medium inside the etalon. At least some of these measures are known as such and therefore need not be further explained here.

Figure 3:
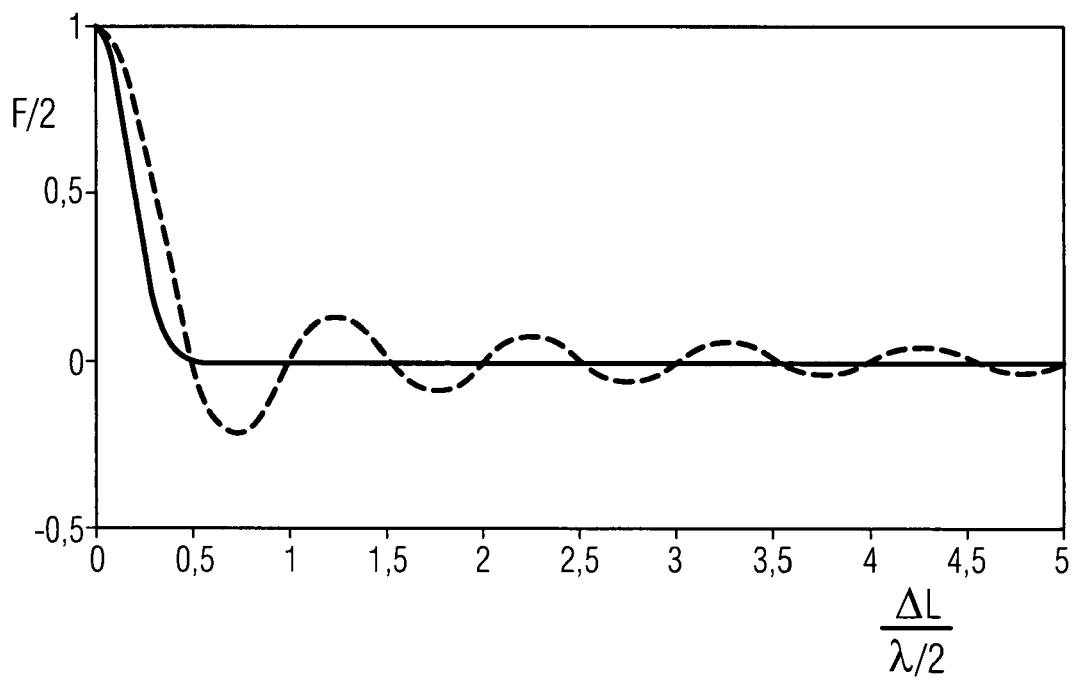
FIG. 3 is a diagram of the interference fringe amplitude as a function of the variation amplitude in case of Gaussian noise modulation (solid line) and triangle modulation (dashed line) and FIG. 4 is a diagram of the interference fringe amplitude as a function of the variation amplitude in case of triangle modulation (solid line) and sinusoidal modulation (dashed line).

FIG. 3 shows the interference fringe amplitude F (peak-to-peak optical fringe depth) as a function of the variation amplitude in case of the Gaussian noise modulation according to the invention (solid line) and, for comparison, the triangle modulation according to the prior art (dashed line). As can be clearly seen, the advantage of the random modulation compared to the triangle modulation is that it is no longer necessary to use vibration amplitudes $\Delta L$ over several laser wavelengths $\lambda$ since an efficient etalon averaging is obtained already at amplitude distribution with a standard deviation a slightly above $\lambda/4$. Another advantage is that, due to character of noise modulation, there is no need of amplitude and phase control of the modulating waveform, thus allowing much simpler hardware design.

Figure 4:
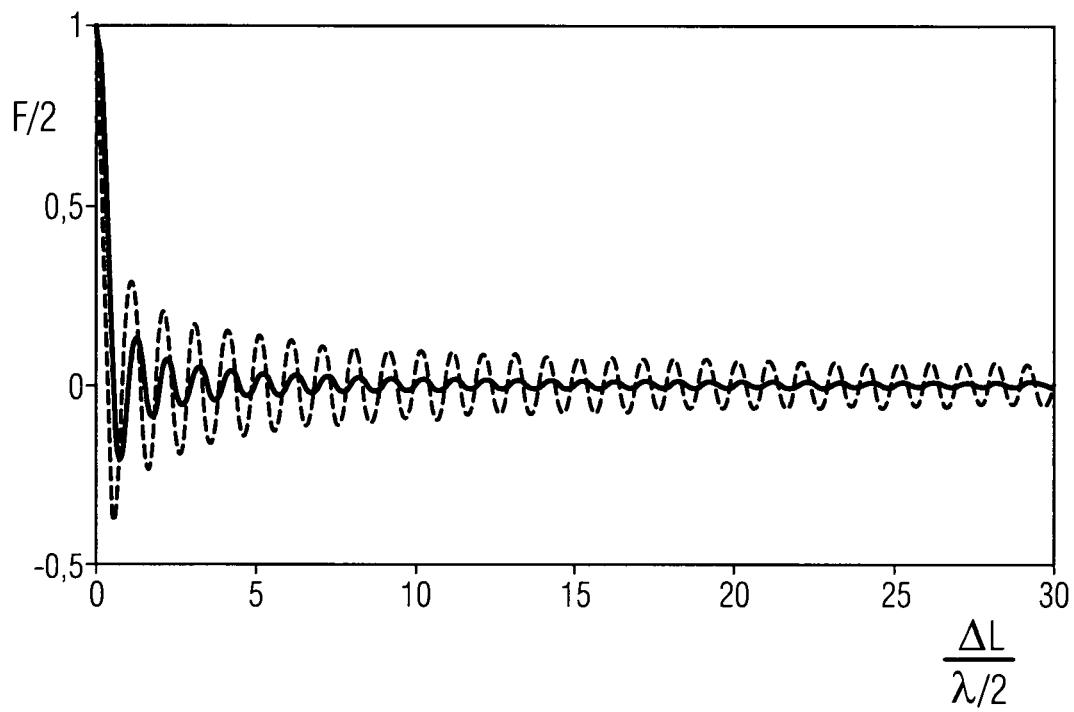

For comparison, FIG. 4 shows the interference fringe amplitude F/2 as a function of the variation amplitude in case of triangle modulation (solid line) and sinusoidal modulation (dashed line). Triangular waveform offers better etalon fringe reduction compared to sinus waveforms since the time spent by the vibrating element at the turning points is minimized. However, the vibration amplitude $\Delta L$ has to be more than 15 laser wavelengths $\lambda$ to obtain a sufficient reduction of the etalon effect.

The invention claimed is:

1. A method for reducing fringe interference of laser light including a wavelength, the interference being created in a passive cavity defined by partially reflecting optical surfaces and the interference including an optical path length, the method comprising:

varying the optical path length of the cavity with random amplitudes following a Gaussian distribution, wherein a standard deviation of the Gaussian distribution is at least one-quarter of the wavelength of the laser light.

2. The method as claimed in claim 1, wherein the standard deviation is at least one-third of the wavelength of the laser light.

3. The method as claimed in claim 1, wherein the standard deviation is less than one wavelength of the laser light.

4. The method as claimed in claim 2, wherein the standard deviation is less than one wavelength of the laser light.

5. The method as claimed in claim 1, wherein along the optical path, one of the optical surfaces of the passive cavity is moved back and forth with random amplitudes following the Gaussian distribution.

6. The method as claimed in claim 1, wherein towards the optical path, one of the optical surfaces is tilted by random degrees following the Gaussian distribution.

7. The method as claimed in claim 1, wherein a tunable optical element comprising a medium with an optical index is placed in the passive cavity, and wherein a thickness of the optical element or an index of the medium is varied with random amplitudes following the Gaussian distribution.

8. An apparatus for reducing fringe interference of laser light including a wavelength, the interference being created in a passive cavity defined by partially reflecting optical surfaces and the interference including an optical path length, comprising:

a device for varying the optical path length of the cavity with random amplitudes following a Gaussian distribution, where a standard deviation of the Gaussian distribution is at least one-quarter of the wavelength of the laser light.

9. The apparatus as claimed in claim 8, wherein the standard deviation is at least one-third of the wavelength of the laser light.

10. The apparatus as claimed in claim 8, wherein the standard deviation is less than one wavelength of the laser light.

11. The apparatus as claimed in claim 9, wherein the standard deviation is less than one wavelength of the laser light.

12. The apparatus as claimed in claim 8, wherein the device for varying the optical length of the cavity comprises an actuator responsive to an electrical signal for varying, along the optical path, the position of one of the optical surfaces of the passive cavity or for varying the angle of one of the optical surfaces towards the optical path; and wherein the device for varying the optical length of the cavity further comprises a noise generator connected to the actuator and generating a Gaussian noise signal as the electrical signal.

13. The apparatus as claimed in claim 11, wherein the device for varying the optical length of the cavity comprises an actuator responsive to an electrical signal for varying, along the optical path, the position of one of the optical surfaces of the passive cavity or for varying the angle of one of the optical surfaces towards the optical path; and wherein the device for varying the optical length of the cavity further comprises a noise generator connected to the actuator and generating a Gaussian noise signal as the electrical signal.

14. The apparatus as claimed in claim 8, wherein the device for varying the optical length of the cavity comprises an optical element arranged in the passive cavity to increase the optical path length by an additional length and wherein the optical element is tunable as to vary the additional length with the Gaussian distribution.

15. The apparatus as claimed in claim 11, wherein the device for varying the optical length of the cavity comprises an optical element arranged in the passive cavity to increase the optical path length by an additional length and wherein the optical element is tunable as to vary the additional length with the Gaussian distribution.

16. The apparatus as claimed in claim 13, wherein the device for varying the optical length of the cavity comprises an optical element arranged in the passive cavity to increase the optical path length by an additional length and wherein the optical element is tunable as to vary the additional length with the Gaussian distribution.

\* \* \* \* \*